United States Patent [19]

Kensey et al.

[11] Patent Number: 4,753,221
[45] Date of Patent: Jun. 28, 1988

[54] BLOOD PUMPING CATHETER AND METHOD OF USE

[75] Inventors: Kenneth Kensey, Hinsdale, Ill.; John Nash, Downingtown, Pa.

[73] Assignee: Intravascular Surgical Instruments, Inc., Frazer, Pa.

[21] Appl. No.: 921,987

[22] Filed: Oct. 22, 1986

[51] Int. Cl.[4] .............................................. A61M 1/03
[52] U.S. Cl. ..................................... 128/1 D; 604/52; 604/151; 415/DIG. 4
[58] Field of Search ................. 604/267, 151, 93, 102, 604/104; 27/24 A, 24 R; 415/DIG. 4, 126–128; 128/1 D

[56] References Cited

U.S. PATENT DOCUMENTS

| | | | |
|---|---|---|---|
| 2,328,199 | 8/1943 | Day | 604/267 |
| 3,568,659 | 3/1971 | Karnegis | 128/1 D |
| 3,864,055 | 2/1975 | Kletschka | 415/DIG. 4 |
| 3,939,820 | 2/1976 | Grayzel | 128/1 D |
| 4,407,271 | 10/1983 | Schiff | 128/1 D |
| 4,493,697 | 1/1985 | Krausc et al. | 604/50 |
| 4,625,712 | 12/1986 | Wampler | 604/151 |

Primary Examiner—C. Fred Rosenbaum
Assistant Examiner—J. L. Kruter
Attorney, Agent, or Firm—Caesar, Rivise, Bernstein, Cohen & Pokotilow

[57] ABSTRACT

An elongated catheter for pumping blood through at least a portion of a being's vascular system. The catheter is of sufficiently small diameter and flexiblility to enable it to be passed through the vascular system so that the distal end portion of the catheter is located within or adjacent the being' heart. A rotatable pump is located at the distal end of the catheter and is rotated by drive means in the catheter. The distal end portion of the catheter includes an inlet for blood to flow therein and an outlet for blood to flow thereout. The catheter is arranged so that blood is pumped by the catheter's pump through the heart and into the vascular system without requiring any pumping action of the heart.

34 Claims, 4 Drawing Sheets

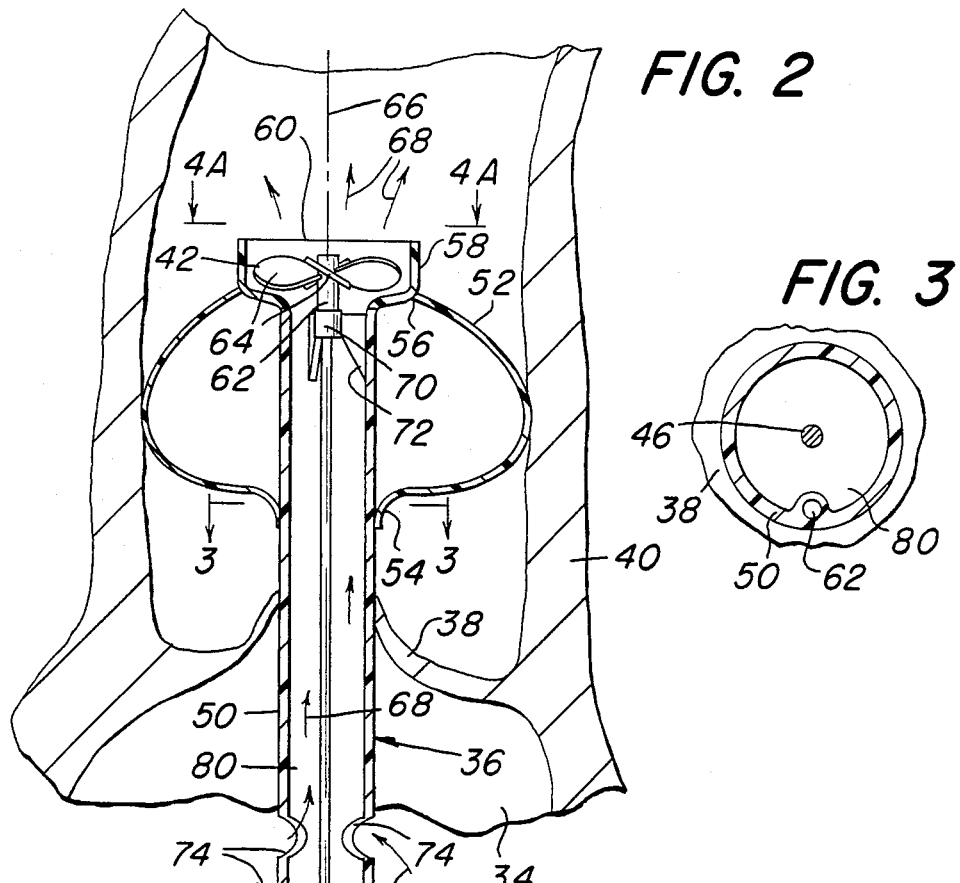

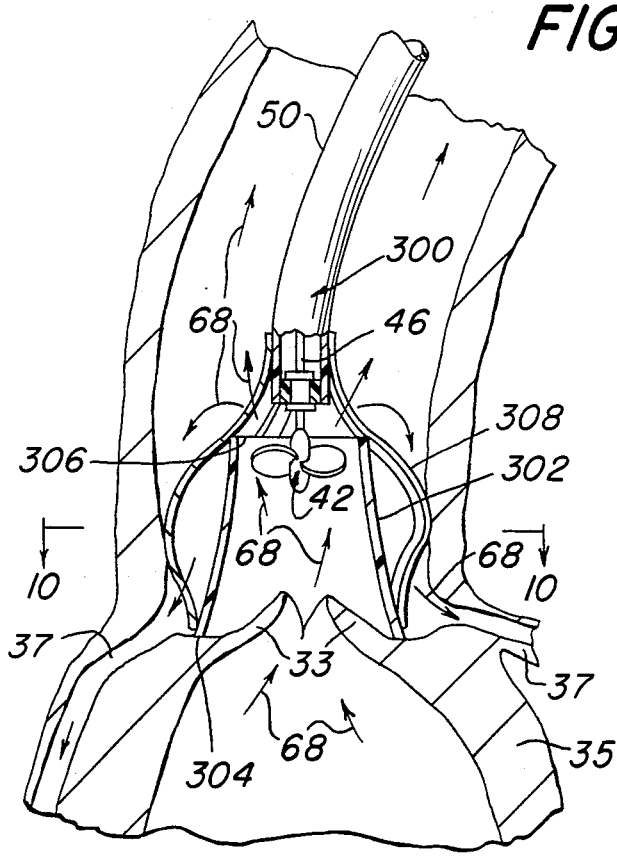
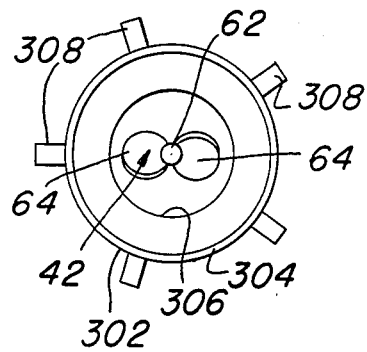
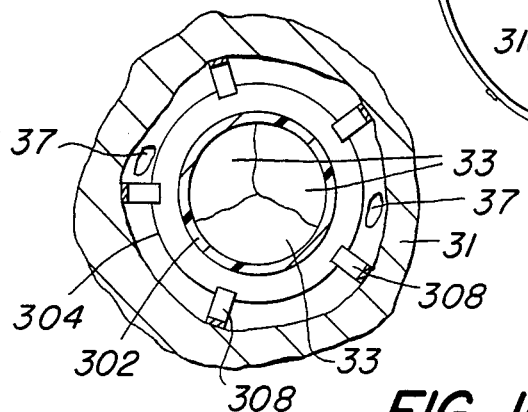
FIG. 7
FIG. 9
FIG. 8
FIG. 10

BLOOD PUMPING CATHETER AND METHOD OF USE

This invention relates generally to medical instruments and more particularly to catheter based instruments for effecting the pumping of blood through the vascular system of a being and methods of using the same.

BACKGROUND OF THE INVENTION

Medical apparatus have been disclosed and are in use today to take over and/or to supplement the action of the heart to effect the pumping of blood into the vascular system. One particularly well known type of apparatus is the so-called "heart-lung" machine. All prior art apparatus for effecting heart pumping action are necessarily complex and expensive. Most significantly such prior art devices are not suitable for general or widespread usage. In this connection, prior art devices invariably require the services of skilled medical personnel, e.g., surgeons, under stringent surgical conditions for effecting the placement, connection and operation of the devices. Accordingly, prior art blood pumping apparatus have not been deemed suitable for general or emergency usage to supplement or replace pumping action of a person's heart. Therefore the need exists to provide apparatus to supplement or replace the pumping action of the heart when a person/animal is undergoing or has just undergone a heart attack or when the person's/animal's heart is otherwise failing and conventional pumping apparatus is not suitable.

OBJECTS OF THE INVENTION

Accordingly, it is the general object of this invention to provide medical apparatus which overcomes the disadvantages of the prior art.

It is a further object of the instant invention to provide minimally invasive medical apparatus for taking over or supplementing the pumping action of the heart.

It is a further object of this invention to provide minimally invasive catheter/pump apparatus which is simple in construction.

It is still a further object of this invention to provide minimally invasive catheter/pump apparatus which is easy and safe to use.

SUMMARY OF THE INVENTION

These and other objects of the instant invention are achieved by providing apparatus for disposition within the body of the being to effect the pumping of blood through at least a portion of the being's vascular system. The apparatus comprises an elongated catheter having a distal end portion. The catheter is of sufficiently small diameter and sufficient flexibility to enable it to be readily passed through a portion of the vascular system so that its distal end portion is located within or closely adjacent the being's heart. The catheter also includes pump means located at the distal end portion and drive means for effecting the operation of the pump means, whereupon blood is pumped by the pump means through the heart and into the vascular system and without requiring any pumping action of the heart.

DESCRIPTION OF THE DRAWINGS

Other objects and many of the attendant advantages of the invention will be readily appreciated as the same becomes better understood by reference to the following detailed description when considered in connection with the accompanying drawings wherein:

FIG. 2 is en enlarged view, partially in section, of the embodiment of the invention shown in FIG. 1A and extending through the pulmonary valve;

FIG. 3 is an enlarged sectional view taken along line 3—3 of FIG. 2;

FIG. 4A is an enlarged end view taken along line 4A—4A of FIG. 2;

FIG. 4B is a side elevational view of the pump portion of the catheter/pump of FIG. 2 but shown in a folded or compact condition prior to operation of the catheter/pump;

FIG. 7 is an alternative embodiment of the catheter/pump shown in FIG. 1B and disposed over the aortic valve;

FIG. 8 is a perspective view of the distal end of the catheter/pump shown in FIG. 7;

FIG. 9 is an end view of the catheter/pump shown in FIG. 7; and

FIG. 10 is a sectional view taken along line 10—10 of FIG. 7.

DETAILED DESCRIPTION OF THE PREFERRED EMBODIMENT

Figure 1A:
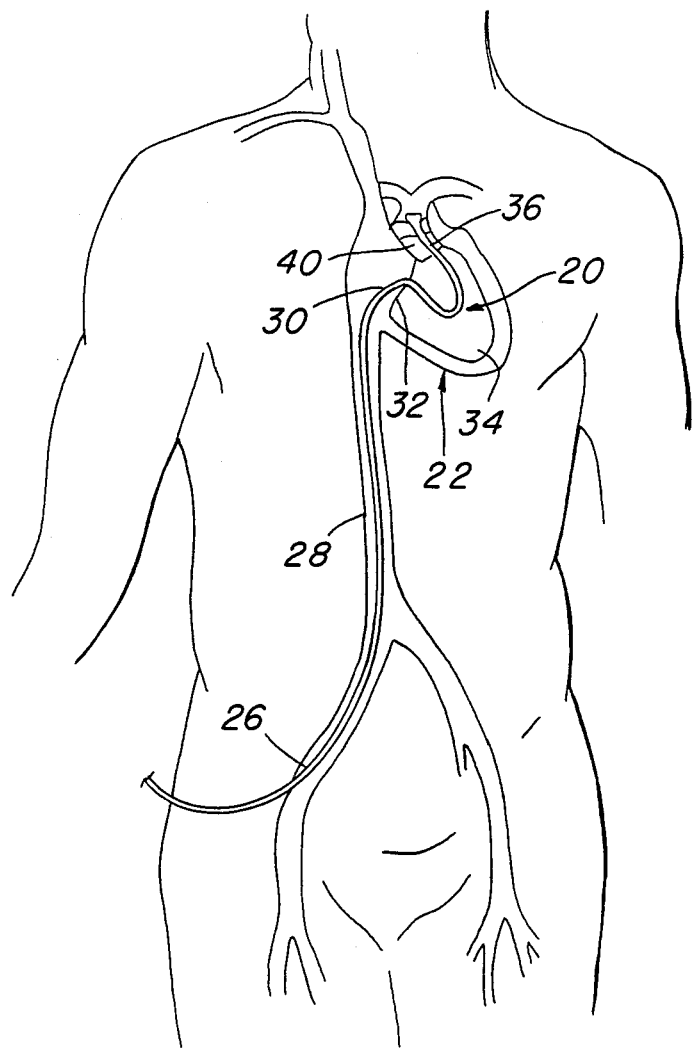
FIG. 1A is an illustration of one embodiment of a catheter/pum constructed in accordance with the subject invention shown located within the right side of a person's heart.
Figure 1B:
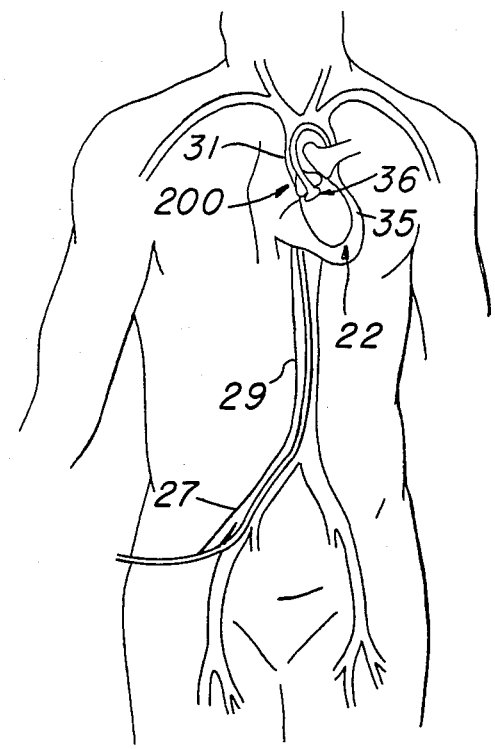
FIG. 1B is an illustration, similar to that of FIG. 1A, but showing the catheter/pump embodiment of FIG. 1A located within the left side of a person's heart.

Referring now in detail to the various figures of the drawing wherein like reference characters refer to like parts, there is shown at 20 in FIG. 1A and at 200 in FIG. 1B catheter/pump devices constructed in accordance with the instant invention. Those devices are arranged to be disposed within the vascular system and heart 22 to effect the pumping of blood through the vascular system.

As will be appreciated by those skilled in the art the catheter/pump devices constructed in accordance with this invention will be different depending upon which portion of the person's heart action is to be replaced or augmented by the operation of the device pump. As is known, the left side of a person's heart pumps blood through the aorta to various portions of the person's body while the right side of the heart pumps blood through the pulmonary artery to the person's lungs. Thus, the left side of the heart does most of the pumping work, typically pumping six liters per minute under a pressure head of up to 100 millimeters of Hg, whereas the right side typically pumps at a pressure head of 12 millimeters of Hg. (20 mm maximum).

In all cases the irrespective of which side of the heart the catheter/pump is to be used in, it comprises an elongated member of small diameter, e.g., 5 to 10 French (1.7-3.3 mm). Moreover, each of the catheter/pumps is sufficiently flexible to enable it to be passed through the vascular system to its desired position within the heart or in its immediate vicinity. The positioning of the catheter/pump device of this invention is carried out through the use of a conventional tubular guide catheter which is first introduced and threaded through the vascular sysftem in a conventional manner.

For example, use of catheter 20 in the right side of the heart is effected by inserting it percutaneously, such as into the illiac 26, through the inferior vena cava, through the right atrium 30, the tricuspid valve 32 and the right ventricle 34 so that the distal end portion 36 of the catheter/pump device 20 extends through the pulmonary valve 38 and into the pulmonary artery 40 immediately above that valve (see FIG. 2).

As can be seen clearly in FIG. 2 the distal end portion 36 of the catheter 20 includes pump means 42. The pump means can take various forms, as will be described later. Suffice for now to state that the pump means is preferably a centrifugal pump which is arranged to be operated, e.g., rotated, by drive means 44. The drive means 44 can take various forms, but preferably comprises the high speed rotary drive system described and claimed in our co-pending U.S. patent application Ser. No. 746,220, filed on June 19, 1985, entitled Spiral Wire Bearing for Rotating Wire Drive Catheter, assigned to the same assignee as this invention, and whose disclosure is incorporated by reference herein. Basically that drive system comprises an elongated drive wire or cable 46 supported in the center of the catheter tube 50, that is, along its central longitudinal axis, by means of a spiral bearing, (not shown). That bearing comprises a helical or spiral coil of wire extending substantially the entire length of the catheter tube from a proximately located point outside the body to the distal end of the catheter. The outer diameter of the helical bearing is sufficiently great so that its loops just clear the interior surface 48 of the catheter tube 50 to hold the bearing securely in place therein. The inside diameter of the central passage extending down the length of the helical bearing is just slightly greater than the outside diameter of the drive cable 46 so the drive cable can rotate freely therein.

In the interests of reducing the size of any wear debris created by the rotation of the drive cable 46 within the spiral bearing, the drive cable may be swaged or drawn to increase the engaging surface area thereof, while the cross-sectional shape of the spiral bearing can be rectangular to also increase the engaging surface area, both of said features being disclosed and claimed in our-copending U.S. patent application Ser. No. 938,698, filed on Dec. 5, 1987, entitled Catheter with Means to Prevent Wear Debris from Exiting, assigned to the same assignee as the instant invention.

The drive cable 46 is arranged to be connected at the proximal end thereof to an electric motor or some other drive means for rotating the cable at a high rate of speed, e.g., from 10,000 to 200,000 rpm, to effect the operation of the pump 42.

As can be seen clearly in FIG. 3, the distal end portion 36 of the catheter is of generally tubular construction, i.e., is an extension of catheter tube 50, and whose outside diameter is the same as the outside diameter of the remainder of the catheter. Disposed adjacent the free end of the distal end portion is a balloon 52. As can be seen the balloon 52 is an annularly shaped member which is fixedly secured at its proximal end 54 about the outer periphery of the catheter's distal end portion 36. The distal end portion of the balloon 52 is denoted by the reference numeral 56 and is also fixedly secured to the distal portion 36 of the catheter adjacent its free end. The free end 58 of the distal end of device 20 is preferably shaped and constructed of a flexible elastomeric material so that when the balloon 52 is fully inflated, as shown in FIG. 2, the free end portion 58 expands outward radially to form an enlarged diameter flared outlet 60. When the balloon is partially inflated or uninflated the flexible end portion 58 flexes back to an unbiased position, wherein its outside diameter is approximately equal to the outside diameter of the catheter tube 50.

As will be described hereinafter the pump 42 is an expandable/contractable member so that when the free end portion 58 of the catheter is expanded, by the inflation of balloon 52, the pump 42 expands from a closed or compact position shown in FIG. 4B to an open and operative position shown in FIG. 2. The inflation of the balloon 52 is effected via a lumen 62 formed in the wall of the catheter tube 50. The lumen 62 extends longitudinally the entire length of the device 20 and terminates at the distal end thereof in a port (not shown) in fluid communication with the interior of balloon 52. Thus, air or some other fluid can be passed through lumen 62 down the catheter and into the interior of balloon 52, thereby inflating the balloon, to expanding the free end of catheter 58. This action enables the pump 42 to automatically open up or expand to the position shown in FIG. 2.

In the embodiment shown in FIG. 2, the pump 42 is an axial type pump basically comprising a central hub 62 from which four blades or impellers 64 extend. The blades are biased to naturally project outward radially. However, the blades are formed of flexible material so that when the free end 58 of the distal end of the device is compacted (unexpanded) the blades are flexed into the closed or compressed position shown in FIG. 4B. When released or freed they extend radially outward from the hub 62. Moreover each of the blades 64 is angled so that when the pump is rotated about the central axis 66 of the device the blades 64 force blood out the outlet 60 in the direction of arrows 68.

The proximal end of hub 62 is connected to the distal end of drive cable 46 so that the rotation of cable 46 causes the concomitant rotation of pump 42.

The edges of each of the blades 64 are preferably rounded so as not to present any sharp edges which could adversely affect the blood cells pumped thereby.

The pump 42 is held in position centered within the device's free end portion 58 by a bearing support 70. The bearing support 70 has a central hub section from which plural arms 74 extend. The arms are secured to the inner surface 48 of the catheter tube 50.

As can be seen in FIG. 2, the distal end portion 36 of catheter 20 also includes a plurality of inlet apertures 74 extending through the catheter tube 50. These apertures are located a sufficient distance proximately of the outlet 60 so that when the device's distal end portion 36 is in the position shown in FIG. 2 the inlet ports 74 are located within the heart's right ventricle outflow track, that is, the portion immediately below the pulmonary valve 36, while the device's outlet 60 is located within the pulmonary artery slightly above the pulmonary valve.

A support bearing 76 is located within a central opening in a thickened wall portion 78 of the catheter tube 50 just proximately of the ports 74. The bearing 76 supports the drive cable 46 for rotation about central axis 66 (i.e., the longitudinal axis of the catheter tube 50) through the distal end portion 36 without necessitating the use of spiral bearing means therein. Thus, the interior of the distal end portion 36 is a virtually unobstructed passageway, denoted by the reference numeral 80.

Operation of the catheter 20 is as follows: the catheter with its balloon 52 only partially inflated is fed through the body so that its distal end portion 36 extends through the pulmonary valve 38. The partially inflated balloon serves to aid in carrying the device to the desired position. When in position, the balloon is then fully inflated by providing air or some other fluid through lumen 62 into the interior of the balloon. This causes the periphery of the balloon to engage the interior surface of the pulmonary artery 40, thereby locking the distal end of catheter/pump 20 in place. Moreover, the expansion of the balloon 52, also causes the flexible free end 58 of the device to expand outward, as shown in FIG. 2, whereupon the pump 42 is unconstrained and, owing to its natural bias, assumes the open position shown in FIG. 2, from the position shown in FIG. 4B.

The drive motor (not shown) is energized, thereby rotating the drive cable 46 and causing the concomitant rotation of pump 42. This action has the effect of pulling blood from the right ventricle into the inlet apertures 74 in the direction of arrows 68. The blood flows down the passageway 80 through the spaces between radially projecting fingers 72 of the bearing support 70 and out through outlet 60 into the pulmonary artery 40.

It should be pointed out at this juncture that when the catheter 20 is used in the right side of the heart the distal end portion 36 must pass sufficiently through the pulmonary valve 38 so that the balloon clears the valve so as not to interfere with its action.

Figure 5:
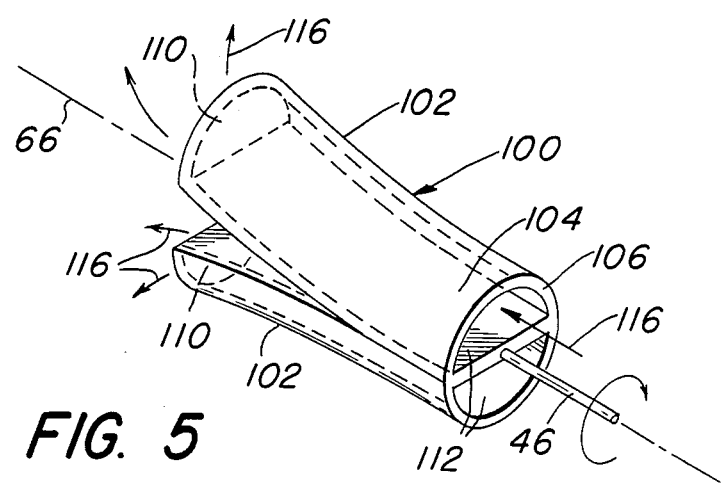
FIG. 5 is an enlarged perspective view of an alternative pump to that shown in FIG. 2.

Referring now to FIG. 5, an alternative embodiment of a pump for use in the catheter 20 is shown. That alternative pump is a centrifugal pump and is denoted by the reference numeral 100. As can be seen, pump 100 basically comprises a generally tubular body composed of a pair of semicircular, tubular arms 102 which are joined together at their distal end 104. Each arm includes a hemicylindrical passageway 106 extending therethrough. The arms 102 are sufficiently flexible so that they can flex or pivot outward as shown in FIG. 5 from a rest position (now shown) when the pump 100 is rotated about its central axis (which is the central axis 66 of the catheter tube 30). Each tubular arm includes an outlet 110 at the distal end thereof and an inlet 112 at the proximal end thereof. The wall portion 114 dividing the pump 100 into the two arms 102 at the proximal end thereof is connected to the distal end of drive cable 46 coaxially with central axis 66.

As should be appreciated by those skilled in the art upon the rotation of drive cable 46 the centrifugal force on the arms 102 cause them to flex outward, thereby creating a centrifugal pumping action to draw blood into the inlet 106 and out of outlets 110 as shown by the arrows denoted by the reference numeral 116. Thus, when the centrifugal pump 100 is used in the catheter 20, its rotation causes blood to flow into the inlet apertures 74, down passageway 80 between the arms 72 of the bearing support 70, into the pump inlets 106 down arms 102 and out through outlet 110 for egress through outlet 60 at the free end of the device 20.

Figure 6:
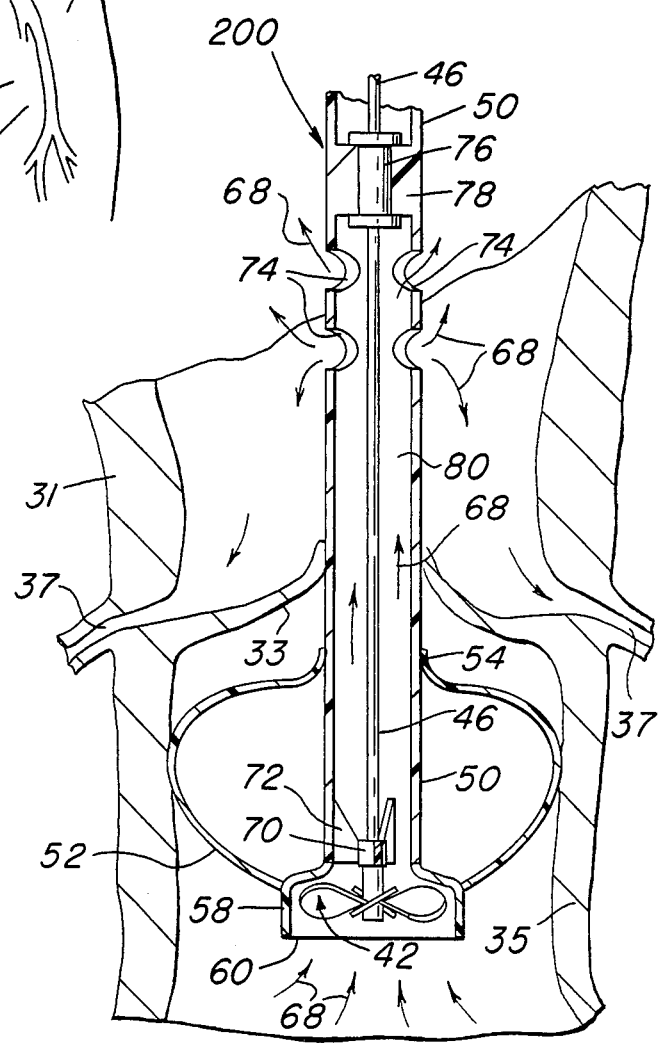
FIG. 6 is an enlarged sectional view of a portion of the catheter/pump shown in FIG. 1B extending through the aortic valve.

Turning now to FIGS. 1B and 6, the disposition of catheter/pump device 200 in the left side of the heart will now be described. As can be seen, device 200 is constructed similarly to device 20, except for its pump (to be described later). The catheter 200 is disposed in the body as follows: it is inserted percutaneously into the femoral artery 27, up through the descending aorta 29 and around and down the aortic arch 31, down the ascending aorta so that the distal end portion 36 of the catheter extends through the aortic valve 33 and into the neck of the left ventricle 35. The balloon 52 is then fully inflated in the manner as described with reference to FIG. 2 to hold the distal end of device 200 in place. As can be seen clearly in FIG. 6, with the device 200 in position as shown, the heart's coronary arteries 37 are not blocked or occluded. Since the device 200 is similar in construction to catheter 20, like reference numerals are used for like parts. However, as will be appreciated by those skilled in the art inasmuch as device 200 is positioned in opposition to the direction of the blood flow (whereas device 20 is positioned in the direction of the blood flow) the blades 64 of the pump means 42 of device 200 are reversed so that the opening 60 at the free end 58 of the catheter, now forms the inlet for the device while the apertures 74 now form its outlet. Thus, upon the rotation of drive cable 46 blood is pulled from the left ventricle 35 into inlet 60 by the rotation of pump 42, the blood flows upward through the passageway 80 and out of the outlet apertures 74 into the aorta 31 and coronary arteries 37. The direction of blood flow is again denoted by the arrows 68.

Like device 20, device 200 can utilize the flexible arm centrifugal pump 100 in lieu of the bladed or propeller-like pump 42. In such an arrangement the pump 100 must be mounted in the appropriate direction within the distal end of device 200.

It also should be pointed out at this juncture that the device 200 may utilize a plurality of outlet apertures 74 extending along its length so that blood can be carried directly through the catheter to a desired downstream location, e.g., adjacent the kidneys.

For some applications, e.g., if the patient's heart has completely stopped or if the patient has a calcified aortic valve, it may not be possible or may be undesirable to pass the catheter/pump device 200 through the aortic valve 33 in the manner as just described. Accordingly, an alternative embodiment of catheter/pump is preferably utilized for such left side heart applications. That alternative catheter/pump device is denoted by the reference numeral 300 and is shown clearly in FIGS. 7–10.

As can be seen therein, the device 300 includes a distal end portion which does not pass through the aortic valve 33 but rather is arranged to cover the valve to allow blood to flow therethrough under pumping action of pump means located within the distal end of the device and while not precluding any blood from flowing into the coronary arteries.

In particular the distal end portion of the catheter/pump 300 includes cover means in the form of a cup-shaped member 302 mounted thereat. The member 302 is formed on an elastomeric material and is flared. Thus, member 302 includes an enlarged diameter open free end 304 located at the distal end thereof and a smaller diameter open end 306 located at the proximal end thereof. The cup-shaped member 302 is mounted on the tubular portion 50 of the catheter at the free end thereof via a plurality of resilient fingers 308. Each finger is formed of a resilient material and is slightly arcuate in shape. The distal end 310 of each of the fingers 308 is fixedly secured to the outer periphery of the cup-shaped member 302 adjacent the flared opening 304 while the proximal end portion 312 of each of said fingers is fixedly mounted to the outer surface of catheter tube 50. Each of the members 308 is biased radially outward so that when unconstrained, the fingers move to the position shown in FIGS. 7-10, thereby expanding the cup-shaped member 302 to the position also shown in those figures. The fingers 308 and the cup-shaped member 302 are arranged to be compressed or contracted radially inward by being disposed within a tubular guide catheter (not shown) during placement of the device 300 in the patient. In particular, the catheter/pump 300 is arranged to be inserted through a conventional tubular guide catheter into the body to the position shown in FIG. 7 and the guide catheter retracted to expose the distal end of device 300. This action enables the resilient fingers 304 to move radially outward to the position shown in FIGS. 7-10, thereby causing the cup-shaped member 302 to also assume the position shoen therein.

As can be seen in FIGS. 7 and 9, pump means 42 is mounted on the distal end of drive cable 46. The pump means 42 can be constructed similarly to the pump means 42 described heretofore, e.g., be a bladed member, or can be constructed similarly to the expanding tube pump 100 described with reference to FIG. 5. In the embodiments shown in FIGS. 7 and 9, the pump means 42 comprises a duly bladed pump having a pair of diametrically opposed blades 64 mounted on a hub 62.

The flared end 304 of the cup-shaped member serves as the inlet to the cup-shaped member 302 while the smaller diameter opening 306 serves as its outlet. As can be seen clearly in FIGS. 7 and 8, when the catheter/pump 300 is in position as shown in FIG. 7 its outlet 306 is in fluid communication with the interior of the aorta. Moreover, the radially extending outward fingers 308 hold the cup-shaped member 302 in place away from the interior walls of the aorta so that spaces are provided between the exterior of the cup-shaped member and the interior of the aorta so that blood may flow unimpeded into the coronary arteries 37. The periphery of the free end 304 of the cup-shaped member 302 serves as a flexible lip which is arranged to be disposed over and engage the cusps forming the aortic valve 33, while permitting the aortic valve's cusps to open, as shown in FIG. 7. Accordingly, when the catheter/pump 300 is in position as shown in FIG. 7 and the drive cable 46 rotated to effect the concommitant rotation of the bladed pump 42, blood is drawn from the left ventricle 35 through the aortic valve 33 into the inlet 304 of the cup-shaped member 302. From there the blood flows out the outlet 306 under the action of the rotating pump 42. The blood flowing out of the outlet flows into the aorta, with some of the blood flowing downward between the arms 308 into the coronary arteries 37. The direction of blood flow as just described being denoted by the arrows being the reference numerals 68.

As will be appreciated by those skilled in the art the catheter/pump 300 is self-seating in operation. In this regard, with the cup-shaped member is expanded and located adjacent the aortic valve 300, but not in contact with it, upon the operation of the pump, the distal end 304 of the cup-shaped member will be drawn into engagemenet on the periphery of the aortic valve by the action of the pump.

The cup-shaped member 302 can be formed of various flexible materials and can be of various shapes so long as it is expandable in diameter, and large enough when expanded so as to enable a substantial portion of the cusps of the aortic valve to fit therein.

It should be pointed out at this juncture that catheter/pumps constructed in accordance with this invention can be disposed at the desired location within the heart or in its immediate vicinity by their introduction at any desired point in the vascular system, and not those points described heretofore. Moreover, various other pump means can be utilized in lieu of those disclosed. Such pump means can be expandable or not, depending upon the quantity of blood to be pumped and the pressure head desired.

As will be appreciated by those skilled in the art the catheter/pumps of the subject invention are quite simple in construction, can be inserted into the operative position within the heart or in its immediate vicinity quickly and easily and without the necessity for skilled surgical techniques. Thus, the subject devices offer a viable means for supplementing or replacing heart pumping action anywhere at any time.

Without further elaboration, the foregoing will so fully illustrate our invention that others may, by applying current or future knowledge, readily adopt the same for use under various conditions of service.

We claim:

1. Apparatus for disposition within the body of a living being to effect the pumping of blood through at least a portion of the being's vascular system, said apparatus comprising an elongated catheter having a distal end portion, said catheter being positionable within the vascular system of said being so that its distal end portion is located at an operative position within or adjacent said being's heart, said catheter including pump means located at said distal end portion, said pump means including a rotatable portion of a predetermined, first configuration, said first configuration being sufficiently compact to enable said catheter to be passed longitudinally through a portion of said vascular system to said operative position, said rotatable portion being alterable in configuration to a second, enlarged configuration at said operative position, and drive means for effecting the rotation of said rotatable portion of said pump means at said operative position such that when said rotatable portion of said pump means is in said enlarged configuration blood is pumped by the rotation of said rotatable portion of said pump means through the heart and into said portion of said vascular system.

2. The catheter of claim 1 wherein said distal end portion includes an inlet for blood to flow therein and an outlet for blood to flow thereout, said inlet being in fluid communication with the right ventricle of the heart and said outlet being in fluid communication with the pulmonary artery.

3. The catheter of claim 2 wherein said pump is a centrifugal pump.

4. The catheter of claim 2 wherein said pump is an axial pump.

5. The catheter of claim 2 wherein said distal end portion extends through the being's pulmonary valve.

6. The catheter of claim 5 wherein said pump is a centrifugal pump.

7. The catheter of claim 5 wherein said pump is an axial pump.

8. The catheter of claim 6 additionally comprising expandable means at said distal end portion for holding said distal end portion in place through said pulmonary valve.

9. The catheter of claim 8 wherrein said pump comprises a member having at least one blade arranged to be rotated by said drive means.

10. The catheter of claim 8 wherein said pump comprises a member having a pair of flexible tubes, each of said tubes having an open free end, said tubes being connected together at a common tubular base, said member having a central axis, said base being arranged to be rotated about said axis to cause said free end of said tubes to flex in a direction having a radially outward component, said tubular base being in fluid communication with said inlet and the free ends of said flexible tubes being in fluid communication with said outlet.

11. The catheter of claim 8 wherein said expandable means comprises a balloon.

12. The catheter of claim 1 wherein said distal end portion includes an inlet for blood to flow therein and an outlet for blood to flow thereout, said inlet being adapted so as to be in fluid communication with the left ventricle of said heart, and said outlet being adapted so as to be in fluid communication with the aorta of said vascular system.

13. The catheter of claim 12 wherein said pump is a centrifugal pump.

14. The catheter of claim 12 wherein said pump is an axial pump.

15. The catheter of claim 12 wherein said distal end portion extends through the aortic valve.

16. The catheter of claim 14 additionally comprising expandable means at said distal end portion for holding said distal end portion in place through said aortic valve.

17. The catheter of claim 16 wherein said pump comprises a member having at least one blade arranged to be rotated by said drive means.

18. The catheter of claim 16 wherein said pump comprises a member having a pair of flexible tubes, each of said tubes having an open free end, said tubes being connected together at a common tubular base, said member having a central axis, said member being arranged to be rotated about said axis by said drive means to cause said free end of said tubes to flex in a direction having radially outward component, said tubular base being in fluid communication with said inlet and said free ends of said flexible tubes being in fluid communication with said outlet.

19. The catheter of claim 16 wherein said pump comprises a member having at least one blade arranged to be rotated by said drive means.

20. The catheter of claim 16 wherein said expandable means comprises a balloon.

21. The catheter of claim 12 wherein said distal end portion additionally comprises means located at said distal end portion for engaging the wall of the aorta for holding said distal end portion in place adjacent the aortic valve of said being.

22. The catheter of claim 21 wherein said pump comprises a member having a pair of flexible tubes, each of said tubes having an open free end, said tubes being connected together at a common tubular base, said member having a central axis and being arranged to be rotated about said axis by said drive means to cause said free ends of said tubes to flex in a direction having a radially outward component, said tubular base being in fluid communication with said inlet and said free ends of said flexible tubes being in fluid communication with said outlet.

23. The catheter of claim 12 additionally comprising cover means, said cover means including said inlet and said outlets, said cover means being arranged for disposition within the aorta and adjacent the aortic valve, whereupon blood can flow from said left ventricle through said aortic valve into said inlet in said cover means and through the outlet in said cover means into the aorta.

24. The catheter of claim 23 wherein said pump is located within said cover means between said inlet and said outlet.

25. The catheter of claim 24 wherein said pump means comprises a member having a pair of flexible tubes, each of said tubes having an open free end, said tubes being connected together at a common tubular base, said member having a central axis about which said member is arranged to be rotated by said drive means to cause said free ends of said tubes to flex in a direction having a radially outward component, said tubular base being in fluid communication with said inlet and said free ends of said flexible tubes being in fluid communication with said outlet.

26. The catheter of claim 24 wherein said rotatable portion of said pump means comprises a member having at least one blade arranged to be rotated by said drive means.

27. The catheter of claim 23 wherein said cover means comprises an elastomeric tubular member.

28. The method of pumping blood into the vascular system of a living being without requiring operation of the being's heart by means of a catheter, said catheter having a distal end at which a pump having a rotatable, blood engaging portion is located, said method comprising the steps of introducing said catheter into and through a portion of the vascular system of said being until said pump means is located at an operative position within or closely adjacent the heart of said being, expanding said rotatable portion of said pump from a compact inoperative configuration to an enlarged, operative configuration at said operative position, and causing said rotatable portion of said pump to rotate while in said enlarged operative configuration at said operative position, whereupon blood is pumped into said system through said heart by said rotation.

29. The method of claim 28 wherein said distal end portion of said catheter comprises an inlet for blood to flow therein and an outlet for blood to flow thereout, and wherein said catheter is positioned so that its distal end portion is located such that said inlet is in fluid communication with the left ventricle of said being and said outlet is in fluid communication with the aorta of said being.

30. The method of claim 28 wherein said distal end portion of said catheter comprises an inlet for blood to flow therein and an outlet for blood to flow thereout, and wherein said catheter is positioned so that its distal end portion is located at a position wherein said inlet is in fluid communication with said right ventricle and said outlet is in fluid communication with the pulmonary artery of said being.

31. The method of claim 29 wherein said distal end portion is extended through the aortic valve.

32. The method of claim 30 wherein said distal end portion is extended through the pulmonary valve.

33. The catheter of claim 1 wherein said catheter is of sufficient flexibility to enable it to be freely passed longitudinally through a portion of the vascular system of said being.

34. The method of claim 30 wherein said catheter is of a small diameter and sufficient flexibility to enable it to be introduced percutaneously and passed through a portion of the vascular system of said being to said operative position.

* * * * *